United States Patent [19]

Slim et al.

[11] Patent Number: 5,463,154
[45] Date of Patent: Oct. 31, 1995

[54] ARSINE AND PHOSPHINES AS ACETYLENE CONVERTER MODERATORS

[75] Inventors: David R. Slim, Houston; Edgar L. Mohundro, Baytown, both of Tex.; Stephen M. Mayo, Stillwater, Okla.

[73] Assignee: Exxon Chemical Patents Inc., Wilmington, Del.

[21] Appl. No.: 263,986

[22] Filed: Jun. 22, 1994

Related U.S. Application Data

[63] Continuation of Ser. No. 881,902, May 12, 1992, abandoned.

[51] Int. Cl.$^6$ .............. C07C 5/03; C07C 7/152; C07C 7/00
[52] U.S. Cl. .............. 585/261; 585/259; 585/850; 585/852; 585/856
[58] Field of Search .............. 585/259, 261, 585/850, 852, 856

[56] References Cited

U.S. PATENT DOCUMENTS

| | | |
|---|---|---|
| 2,268,454 | 12/1942 | Kucher . |
| 2,381,198 | 8/1945 | Bailey et al. ............ 260/683.15 |
| 2,837,587 | 6/1958 | Hogan et al. ............ 260/683.15 |
| 3,453,302 | 7/1969 | Pregaglia et al. . |
| 3,463,830 | 8/1969 | Dunning et al. . |
| 3,574,716 | 4/1971 | Coffey et al. . |
| 3,697,448 | 10/1971 | Johnson et al. ............ 252/464 |
| 3,697,615 | 2/1971 | Hughes . |
| 3,900,526 | 8/1975 | Johnson et al. ............ 260/681.5 |
| 3,917,737 | 11/1975 | Yoo . |
| 4,227,025 | 10/1980 | Montgomery ............ 585/259 |
| 4,377,503 | 3/1983 | Dessau . |
| 4,593,148 | 6/1986 | Johnson et al. . |
| 4,605,812 | 8/1986 | Nowack et al. . |
| 4,645,849 | 1/1985 | Lewis . |
| 5,059,732 | 10/1991 | Cosyns et al. ............ 585/259 |

FOREIGN PATENT DOCUMENTS

| | | |
|---|---|---|
| 66287 | 12/1982 | European Pat. Off. . |
| 2588197 | 10/1985 | France . |
| 1182353 | 2/1966 | United Kingdom . |
| 1121643 | 1/1967 | United Kingdom . |
| 1285871 | 6/1968 | United Kingdom . |
| 1154937 | 6/1969 | United Kingdom . |
| 1378747 | 1/1971 | United Kingdom . |
| 2171719 | 2/1985 | United Kingdom . |

Primary Examiner—Anthony McFarlane
Assistant Examiner—Nhat D. Phan
Attorney, Agent, or Firm—Linda K. Russell

[57] ABSTRACT

A method for acetylene hydrogenation which involves adding a member selected from the group consisting of arsine and phosphine to moderate the activity of acetylene hydrogenation catalysts while maintaining acceptable catalyst activity and avoiding the risk of product quality contamination by the acetylene converter moderator. The acetylene hydrogenation process involves adding arsine at a concentration level within the range of about 1 wppb-3 wppb to the gas, such as ethylene, containing acetylene to prevent temperature runaway during the exothermic acetylene hydrogenation reaction. By controlling the presence of arsine levels to such a relatively low level, temperature runaway during the highly exothermic acetylene hydrogenation reaction is prevented while maintaining acceptable catalyst activity levels for purposes of the acetylene hydrogenation reaction.

26 Claims, 3 Drawing Sheets

ARSINE AND PHOSPHINES AS ACETYLENE CONVERTER MODERATORS

This is a continuation of application Ser. No. 07/881,902, filed May 12, 1992, now abandoned.

BACKGROUND OF THE INVENTION

1. Field of the Invention

The present invention relates to the production of ethylene. In particular, the present invention relates to the production of ethylene which is substantially free of acetylene.

Specifically, the present invention is directed to minimizing contamination of ethylene by acetylene produced by steam cracking. To this end, the present invention is directed to selective acetylene hydrogenation over a palladium catalyst wherein a moderator selected from the group consisting of arsine and phosphine is added as an acetylene converter moderator.

2. Discussion of Background Information

It is generally known that high levels of arsine tend to poison acetylene converter catalysts.

For example, U.S. Pat. No. 4,227,025, MONTGOMERY, is directed to a process for the removal of acetylene from cracked gases obtained from conversion processes in which crude oil containing minor amounts of arsenic are thermally or catalytically cracked, hydrocracked, or otherwise subjected to modification resulting in the production of gases containing arsenic. More specifically, U.S. Pat. No. 4,227,025 discloses that arsenic-poisoned palladium catalysts may be regenerated in place by providing a purging step with an arsenic-free gas under acetylene removal conditions into contact with the hydrogenation catalyst, for example, a noble metal catalyst, such as palladium, until the activity and selectivity for removal of acetylene has been restored to the catalyst.

It is also known to hydrogenate acetylenes using homogeneous catalysts that involve phosphine or arsine ligands.

U.S. Pat. No. 2,268,454, ALLIED CHEMICAL CORP., discloses that complexes of anionic group VIII metal (first or second transition series), and hybrid complexes having 1–3 ligands per metal atom, are useful as catalysts in the homogenous hydrogenation of aldehydes, ketones, olefins and alkynes.

U.S. Pat. No. 4,645,849, GENERAL ELECTRIC CO., is directed to the hydrogenation of unsaturated hydrocarbons compounds using cyclo-metallated ruthenium and known transition metal catalysts to provide high conversion rates.

U.S. Pat. No. 3,574,716, IMPERIAL CHEMICAL INDUSTRIES, LTD., is directed to the hydrogenation of an olefin, acetylene, aldehyde, or ketone carried out in the presence of an iridium trihydride complex with 2–3 moles of trihydrocarbon phosphine, -arsine, or stibine, or trihydrocarbon phosphite, arsenite, or antimonite.

British Patent No. 1,121,643, IMPERIAL CHEMICAL INDUSTRIES, LTD., is directed to hydrogenating olefinically or acetylenically unsaturated compounds in the liquid phase in a solution of rhodium complex containing rhodium, anion, and a triorganoarsine, -stibine, or -phosphine, in a 1:1 to 1:4 mole ratio.

British Patent No. 1,154,937, IMPERIAL CHEMICAL INDUSTRIES, LTD., is directed to hydrogenating an unsaturated organic substrate in an homogenous liquid medium in the presence of a zerovalent platinum or palladium compound containing one or more organophosphines.

U.S. Pat. No. 3,463,830, IMPERIAL CHEMICAL INDUSTRIES, LTD., is directed to hydrogenating an unsaturated hydrocarbon in an inert homogenous liquid medium containing a zerovalent platinum or palladium compound having organo-phosphine ligands.

British Patent No. 1,285,871, IMPERIAL CHEMICAL INDUSTRIES, LTD., discloses the use of tetrahydridoaluminates of group IVA or VIII transition metals in which at least one anionic ligand $AlH_4$ is bound to the metal, together with further ligands as are required to satisfy valence and coordination requirements as catalysts, in a wide variety of organic reactions including hydrogenation, polymerization and olefin isomerization, and that such catalysts are particularly useful in catalyzing the hydrogenation of olefins and acetylenes under ambient conditions.

British Patent No. 1,182,353, MONTECATINI EDISON S.p.A., discloses that cobalt hydrocarbonyls are useful as active hydrogenation catalysts for hydrogenation of saturated and unsaturated aldehydes, ketones, alkenes, and alkynes in hydrocarbon solutions.

U.S. Pat. No. 3,453,302, MONTECATINI EDISON S.p.A., discloses that trialkylphosphine-cobalt hydrocarbonyls are useful as catalysts in the hydrogenation of alkenes, alkynes, ketones and aldehydes.

U.S. Pat. No. 3,697,615, PHILLIPS PETROLEUM CO., discloses that olefin or acetylene may be hydrogenated in the presence of a mixture of (a) a rhodium or iridium halide complex, and (b) an Al or B halide compound, wherein the complex suitable for this purpose may be bis(triphenylphosphine)- or bis(trimethylarsine) carbonylchororhodium with a co-catalyst being $AlCl_3BI_3$, or $EtAlCl_2$.

French Patent No. 2,588,197, POUDRES & EXPLOSIFS, discloses a catalyst for the hydrogenation of ethylenic or acetylenic bonds which comprises a coordination metallic complex of which at least one ligand is a tert phosphine.

European Patent No. EP-66-287, WACKER CHEMIE GmbH, discloses that catalysts containing, for example, tris(tert.butyl) phosphine, are active catalysts for hydrogenation of C—C double and triple bonds.

British Patent No. 2,171,719, is directed to the hydrogenation of alkynes to alkenes.

U.S. Pat. No. 3,917,737 discloses the hydrogenation of various unsaturated hydrocarbons, including acetylenes, with complexes of FeCo or Ni catalysts carried on oxide supports, which are typically silica-alumina, wherein the complexes normally include phosphine or donor ligands.

British Patent No. 1,378,747 uses silica-supported noble metal complexes as hydrogenation catalysts for various types of unsaturation, including acetylenes.

Thus, the use of phosphines and arsines in complexes used for hydrogenation appear to be generally known inasmuch as ligands confer essential stability on the complex.

U.S. Pat. No. 4,377,503, DESSAU, is directed to a shape-selective zeolitic catalyst useful for various purposes, including hydrogenation of acetylenes. DESSAU discloses that shape-selective characteristics can be imparted to the metal containing catalysts by reducing a metal containing zeolite in the presence of one or more unsaturated compounds; and that selectivity can be increased, for example, by means of high temperature hydrogen treatment of the zeolite. Shape selectivity of the catalyst can be increased by selectively poisoning the catalyst with a "bulky" poison, such as tri-p-tolylphosphine, which is described as being larger than the pore size of the zeolite, and thus deactivates the metallic catalyst component on the "outside" of the catalyst composite to a greater extent than such poisons would poison the metal function in the interstices of the composite.

In general, however, arsine is considered to be a poison for catalysts used in selective hydrogenation of acetylenes.

As indicated above, U.S. Pat. No. 4,227,025, PHILLIPS PETROLEUM CO., is directed to the removal of acetylene from ethylene using catalysts which are periodically reactivated after being poisoned by the arsenic.

is

U.S. Pat. No. 4,605,812, PHILLIPS PETROLEUM CO., also directed to removing arsenic impurities, such as hydrocarbyl arsines, from hydrocarbon streams in order to remove the arsine impurities from the hydrocarbon stream effluent with a noble metal hydrogenation catalyst to hydrogenate the olefin present therein.

U.S. Pat. No. 4,593,148, PHILLIPS PETROLEUM CO., is directed to the removal of arsine from gases, for example, by contacting with sorbent comprising copper oxide and zinc oxide, to remove arsine impurities for the purpose of preventing catalyst poisoning by $AsH_3$ and/or hydrocarbyl arsines in a hydrocarbon feedstream, for example, $C_{2-6}$ olefin streams, prior to hydrogenation of acetylenic impurities on noble metal catalysts.

An MDA analyzer model 7100 supplied commercially by MDA Scientific, Lincolnshire, Ill., is a continuous toxic gas monitor which, in the Serials 7100, is disclosed as being useful for ammonia, chlorine, diisocyanates, hydrazines, hydrides, hydrogen chloride, hydrogen cyanide, hydrogen fluoride, hydrogen sulfide, nitric acid, nitrogen dioxide, p-phenylene diamine, phosgene, and sulfur dioxide. As advertised, the Series 7100 continuous toxic gas monitors are capable of detecting concentrations as low as 1 ppb.

The British standard method for the determination of arsenic is disclosed in British Standards Publication BS4404 and is also referred to as the silver diethyldithiocarbamate procedure for the determination of arsenic.

SUMMARY OF THE INVENTION

In general, therefore, the present invention is based on the discovery that arsine and phosphine can be used to moderate the activity of acetylene hydrogenation catalysts while maintaining acceptable catalyst activity, enhancing the acetylene hydrogenation selectivity to ethylene, and avoiding the risk of product quality contamination.

In the production of ethylene, the presence of acetylene is undesirable. As indicated above, however, one of the by products from steamcracking is acetylene. Therefore, there has been a general concern for minimizing the presence of acetylene in ethylene and conventional procedures which have been proposed to eliminate the deleterious effects of the presence of acetylene in ethylene include the selective hydrogenation of acetylene over a palladium catalyst. However, inasmuch as acetylene hydrogenation is a highly exothermic reaction, it has been necessary to add a moderator during the reaction to enhance selectivity. A conventional acetylene converter moderator is carbon monoxide which is typically employed for this purpose. Normally, carbon monoxide is added at concentrations within the range of about 1 ppm–5 ppm which acts as a temporary poison. However, it has been observed that the carbon monoxide does not remain on the catalyst surface but ends up in the product ethylene. This is unacceptable inasmuch as carbon monoxide is a recognized poison and carbon monoxide contamination of product ethylene can be a problem for downstream polymerization processes, e.g., high density polyethylene (HDPE) and linear low density polyethylene (LLDPE) processes.

The present invention, therefore, is based on the discovery of acetylene converter moderators which are selected from the group consisting of substances which remain on the catalyst surface and do not migrate into the product ethylene stream. The acetylene converter moderators more preferred for purposes of the present invention are selected from the group consisting of arsine and phosphine, with arsine being the most preferred acetylene moderator.

As previously mentioned, however, it is generally known that arsine tends to poison acetylene converter catalysts. Thus, the discovery of the present invention, i.e., that arsine and phosphine can be effectively used as acetylene converter modifiers, is particularly unexpected.

In this regard, and in accordance with the present invention, arsine is used at a relatively low level within a concentration range which has been found to be effective for maintaining acceptable catalyst activity and enhancing selectivity to the desired extent.

In accordance with the present invention, the unexpected results of the present invention can be achieved by using arsine at a concentration within the range of about 0.01 wppb–10 wppb.

Although not wishing to be bound by any particular theory, it is believed that arsine and phosphine function unexpectedly when used in the stated concentrations as acetylene converter moderators because arsine and phosphine remain on the catalyst, rather than being transferred into the product stream, so that they do not tend to poison the LLDPE systems.

Moreover, inasmuch as arsine is used at concentrations within the range of 0.01 wppb–10 wppb, such lower concentrations render arsine safer to use than conventional acetylene converter moderators, such as carbon monoxide.

Therefore, the use of arsine and phosphine as acetylene converter moderators is believed to be novel and unobvious because arsine and phosphine are generally considered to be severe poisons of acetylene hydrogenation systems in view of the fact that systems are normally put into place to remove arsine from the reaction zone in some fashion.

More specifically, the present invention is directed to a process for removing acetylene from a hydrocarbon stream, which involves exposing a hydrocarbon stream comprising acetylene to an hydrogenation catalyst in the presence of an amount of acetylene converter moderator which substantially remains on said hydrogenation catalyst and does not substantially migrate into said hydrocarbon stream under conditions effective to support acetylene hydrogenation with enhanced selectivity.

For purposes of the present invention, the stream includes a member selected from the group consisting of ethylene, and a mixture of ethylene and ethane.

In accordance with the present invention, the acetylene converter moderator is preferably selected from the group consisting of arsine and phosphine, and is most preferably arsine.

For purposes of the present invention, arsine is preferably present in an amount within the range of about 0.01 wppb to about 10 wppb, and most preferably within the range of about 1 wppb to about 3 wppb.

In accordance with the present invention, the hydrogenation catalyst is exposed to arsine by blending up to 1000 wppm arsine in a carrier gas, preferably using a technique selected from the group consisting of a direct external injection technique and a controlled leakage technique.

Most preferably, the technique is direct external injection, wherein an amount less than about 400 ppm arsine is blended with the carrier gas, wherein the amount is more preferably within the range of 10 ppm–400 ppm, and most preferably is about 200 ppm.

For purposes of the present invention, the carrier gas is selected from the group consisting of ethylene, ethane, nitrogen, helium, and argon and mixtures thereof, and preferably is selected from the group consisting of argon and ethylene.

The process of the present invention preferably involves contacting the hydrogenation catalyst with the carrier gas containing about 100 wppm–20,000 wppm acetylene at a temperature with the range of about 80° F. to about 350° F., a pressure within the range of about 100 psi to about 750 psi and at an gas hourly space velocity of about 3000 v/hr./v. to about 15,000 v/hr./v. to control the amount of arsine on the hydrogenation catalyst to within the range of about 1 wppb to about 3 wppb.

The process of the present invention also involves regenerating the deactivated catalyst to restore at least some of the loss of catalyst activity due to coking, green oil formation or combination of coking and green oil formation, in addition to repeating the regeneration of the catalyst successively until the catalyst activity is reduced to an unacceptable level due to coking, green oil formation, or a combination of coking and green oil formation. For purposes of the present invention, unacceptable level of catalyst selectively loss due to coking, green oil formation or the combination of coking and green oil formation occurs before a permanent poisoning by arsenic.

For purposes of the present invention, the hydrogenation catalyst includes a transition metal selected from the group consisting of Group VIII metals, Group VIIIA metals and IB metals, preferably wherein the metal is palladium, which is based on a support, which is composed of a support material selected from the group consisting of silica, zeolite, alumina, and a combination thereof, which is most preferably alumina.

Although not wishing to be bound by any particular theory, it is believed that regenerating results in transferring arsenic from palladium sites to the alumina.

In accordance with the present invention, the hydrocarbon stream comprises catalytic cracker gas, steam cracker gas, ethylene and acetylene and is produced by a procedure selected from the group consisting of stream cracking, catalytic coking, wherein the conditions effective to support acetylene hydrogenation include a temperature within the range of about 80° F. to about 350° F., pressures within the range of about 100 psi to about 750 psi, and hourly space velocities within the range of about 3,000 to about 15,000 v/hr./v.

The present invention is also directed to an ethylene product which is substantially devoid of acetylene and substantially devoid of at least one member selected from the group consisting of carbon monoxide, arsine, and phosphine, and is most preferably substantially devoid of carbon monoxide.

The present invention is also directed to a method of producing an ethylene product which involves providing ethylene which is substantially devoid of acetylene and acetylene converter moderators; and processing such ethylene to produce a product comprising said ethylene.

DETAILED DESCRIPTION

As previously discussed, the presence of acetylene in, for example, ethylene is undesirable. Therefore, the present invention is directed to a new and unobvious method relating to minimizing the presence of acetylene in ethylene.

More specifically, the present invention is directed to a process for the catalytic and selective removal of acetylene from a gas, for example ethylene, containing acetylene in the presence of a hydrogenation catalyst, such as a noble metal, for example, palladium, by passing the ethylene containing the acetylene together with an inert gas containing an amount of an acetylene converter moderator selected from the group consisting of arsine and phosphine to prevent temperature runaway while maintaining acceptable activity of the hydrogenation catalyst with which it comes into contact during acetylene hydrogenation.

In accordance with the present invention, the hydrogenation catalyst is exposed to arsine in a concentration within the range of 0.01 wppb–10 wppb by blending a high concentration of arsine in an inert gas, such as argon.

Figure 1:
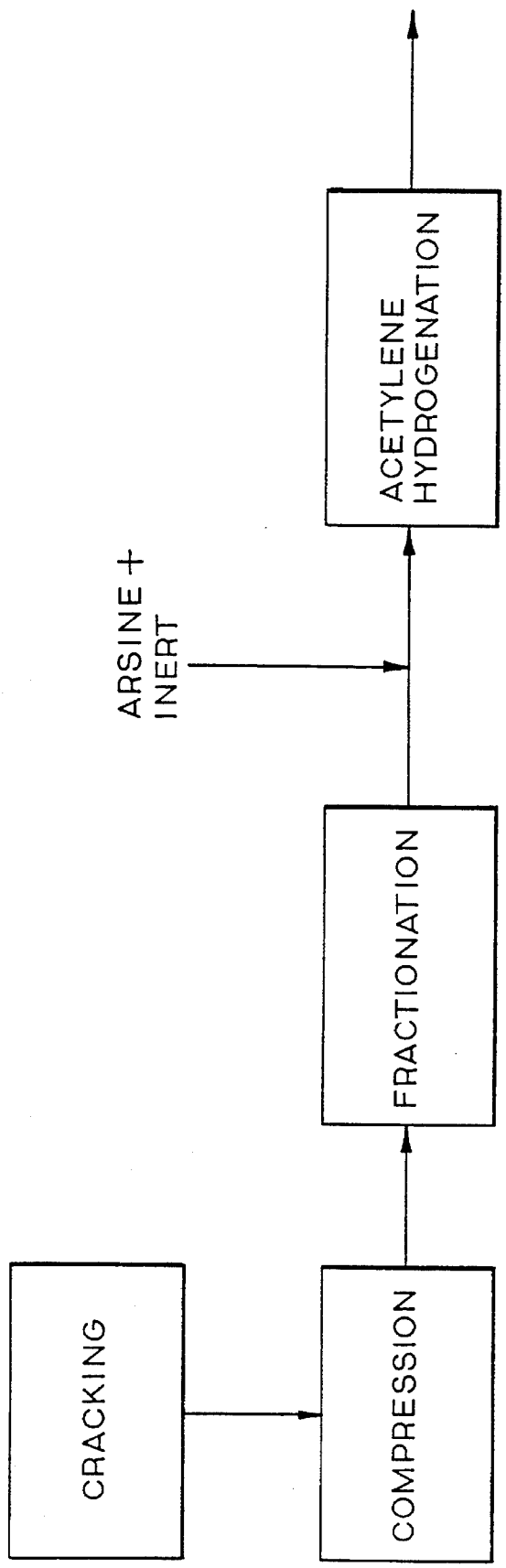
FIG. 1 is a flow chart for the process of the present invention.
Figure 2:
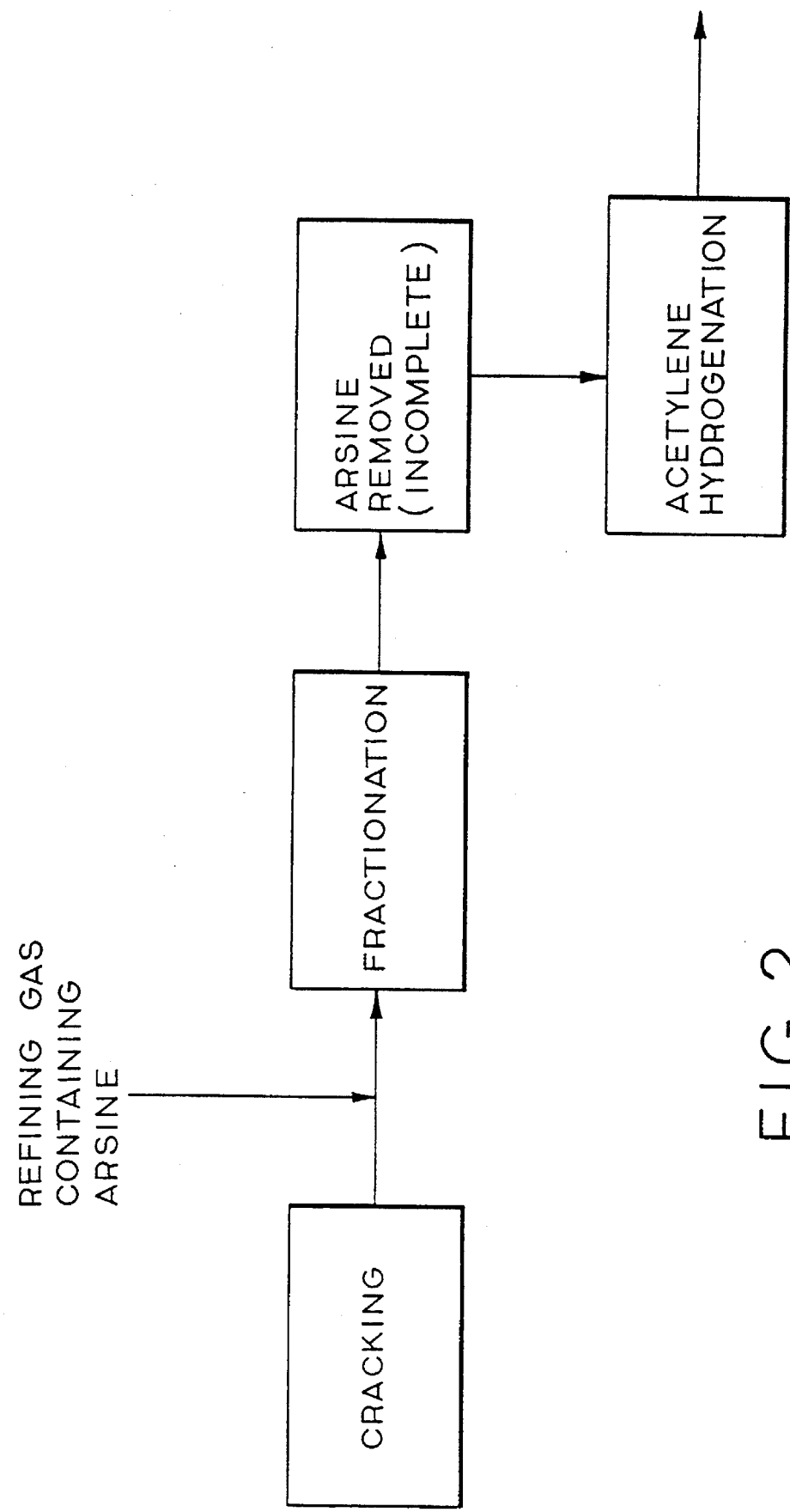
FIG. 2 is a flow chart for an alternative process of the present invention.

In general, the present invention can be practiced by having 0.1–10 wppb arsine in the feed to the acetylene hydrogenation unit. The preferred way of controllably achieving 0.1–10 wppb arsine in the feed is through the instrumented computer controlled, i.e., injection of a small stream of arsine blended in an inert gas, for example, as shown in FIG. 2. The preferred level of arsine is within the range of about 1 wppb to about 3 wppb, and this value is controlled to achieve optimum selectivity throughout operation between regenerations.

As the catalyst "ages" through combination of on-stream operation and successive regenerations, the level of required arsine may be varied. For illustration, when operating with new catalyst, the level of arsine in the converter feed should be about 5 ppb to achieve nearly optimum selectivity. However, after the catalyst has been subjected to three or more regenerations, the preferred level of arsine may decline to about 1 ppb–3 ppb.

Also, trace amounts of arsine, in the feed to the acetylene hydrogenation unit can be achieved by processing of arsine containing streams within the ethylene plant process upstream of the acetylene hydrogenation unit. An example of this would be where an arsine containing refinery gas stream, i.e., $C_3$ and higher, is mixed into the ethylene plant process gas from the steam cracking furnaces.

More specifically, the process of the present invention involves contacting a gas, such as ethylene containing acetylene and arsine in concentrations within the range of 0.01 wppb–10 wppb under conditions to permit hydrogenation of the acetylene, i.e., under controlled acetylene removal conditions, with an appropriate hydrogenation catalyst, for example, a noble metal catalyst such as palladium, until the activity of the catalyst for acetylene removal has been undesirably reduced as a result of deactivation or activity loss by coking and/or green oil formation.

Although the prior art, for example, as disclosed in U.S.

Pat. No. 4,227,025, indicates that the presence of arsine in the gas otherwise composed of ethylene and acetylene will cause the hydrogenation catalyst to become severely deactivated, it has been unexpectedly discovered that this is not the case where, in accordance with the present invention, arsine is used at concentrations within the range of 0.01 wppb–10 wppb in accordance with the method of the present invention as described herein.

For purposes of the present invention, therefore, it is important to precisely control the amount of arsine to within the range of 0.01 wppb–10 wppb which requires extremely sensitive and accurate analytical techniques. In accordance with the present invention, it was discovered that three analytical techniques are preferred for detecting trace levels of phosphine and arsine required to practice the present invention. The analytical techniques preferred for purposes of the present invention are:

a) The MDA analyzer model 7100 lab model 8500 on-line
This analyzer is supplied commercially by MDA Scientific, Lincolnshire, Ill.

b) The Silver diethyldithiocarbamate method is a slightly modified form of British Standards Method BS 4404; 1968

For purposes of the present invention, inasmuch as the gas is arsine, then the potassium iodide/stannous chloride followed by zinc and acid may be deleted from the standard procedure otherwise described in BS 4404; 1968, because these steps would convert organic arsenic to arsine. By passing high volumes of gas through the silver diethyldithiocarbamate solution, low detection levels can be obtained.

Thus, in contrast to what is taught or suggested by the prior art, it has been unexpectedly discovered that at such low levels, arsenic does not appear to build up on the palladium sites causing catalyst deactivation. Although deactivation of the catalyst may occur to some extent, activity loss which results in the deactivation of the catalyst is believed to be a result of coking and/or green oil formation.

In this regard, it has been discovered that hydrogenation catalysts suitable for purposes of the present invention can tolerate an amount up to about 2 wt. % arsenic before permanent deactivation occurs.

For purposes of the present invention, such low levels of arsenic can be detected by the following procedure:

Fresh Pd on $Al_2O_3$ catalyst was impregnated with arsenic to a variety of concentrations by contacting the catalyst with an aqueous solution of arsenic pentoxide and drying. Each impregnated catalyst was regenerated in a muffle furnace to simulate transfer of arsenic to the base. The acetylene hydrogenation ability of each regenerated catalyst was determined by passing a gas containing acetylene, hydrogen, ethylene, and nitrogen, activity as a function of temperature.

The results are tabulated below:

TABLE 1

Effect of Arsenic Loading on Catalyst Activity

| Activity temperature (°C.) for 90% Acetylene Removal | Arsenic loading on Catalyst |
|---|---|
| 57 | 0.0 |
| 58 | 0.25 |
| 60 | 0.80 |
| 64 | 1.15 |
| 67 | 1.25 |
| 68 | 1.40 |

The results indicate that no activity loss was observed until the arsenic concentration exceeded 0.75 wt.%. Above this level, the activity dropped rapidly. When the loading reached 2% the activity has been determined to be unacceptable for a commercial operation.

As a practical matter, it has been discovered that the catalyst activity will reach an unacceptable level as a result of successive regenerations before the catalyst will become permanently poisoned by the arsenic as a result of treatment in accordance with the present invention. In this regard, lab simulations show that following regeneration, permanent loss in activity starts to occur at arsenic loadings above 0.75 wt %, and becomes very significant at 2 wt % loading.

For purposes of such simulations in accordance with the present invention, the following procedure was used.

An acetylene containing gas blend was fed at a known flow rate from a cylinder to the reactor. Inside the reactor was an arsenic promoted palladium on alumina catalyst. Each batch of catalyst was prepared by contacting the catalyst with an aqueous solution of arsenic pentoxide, evaporating the residual water, drying and regenerating at 450° C. in air. The gas rate was chosen such that the space velocity was 5000 v/hr/v. The products from the reactor were analyzed via GC to determine the extent of acetylene hydrogenation.

In a typical experiment, the extent of acetylene removal was determined as a junction of reactor temperature and arsenic content on the catalyst bed. The relative catalyst activity was then determined as a function of the arsenic loading.

In accordance with the present invention, the gas, e.g., ethylene containing acetylene and arsine in concentrations within the range of about 0.01 wppb to about 10 wppb under controlled acetylene removal conditions, is contacted with an appropriate hydrogenation catalyst preferably by either an external injection of arsine/phosphine technique or a controlled leakage of indigenous arsine through an arsine removal bed. In either case, the process parameters are essentially the same, the main difference being the manner the arsine enters the gas stream to the acetylene converter. The converter operating conditions are:

| feed composition | acetylene 1.0% |
|---|---|
| ethylene | 65.0% |
| ethane | 34.0% |
| arsine | 2 ppb |
| catalyst | 0.03% Pd on $Al_2O_3$ |
| temperature | 120° F. |
| pressure | 300 psig |
| space velocity | 3000 v/hr./v |

For the direct injection technique, arsine is injected into the process stream from cylinders containing 200 ppm Arsine in ethylene at a controlled rate such that the 2 ppb concentration in the process gas is achieved.

For the controlled leakage technique, an upstream arsine removal bed, i.e., PbO an $Al_2O_3$, is operated in such a manner as to allow 2 ppb Arsine to leak into the process stream as measured by an on-line analyzer.

In both cases, the acetylene converter operates at high selectivity, i.e., 0.75% absolute ethylene gain and acceptable catalyst activity.

In an alternative embodiment for practicing the present invention, for example, as shown in FIG. 2, the refining gas-containing arsine is introduced into the stream upstream of the fractionation stage.

Although two alternative processes have been illustrated for purposes of explaining the invention for the better understanding of those skilled in the art, it should be noted that there are several variations on such schemes with respect to the location of the refinery gas injection, $H_2S/CO_2$ clean-up of the refinery gas and the like which could be used without departing from the spirit and scope of the present invention as disclosed and claimed herein. Thus, the processes depicted in the Figures should only be construed to be non-limiting examples which are given by way of illustration of the present invention, and are not offered with any indication that the present invention is strictly limited in accordance with such processes.

Once the activity of the catalyst is observed as being reduced, for example, by coking and/or green oil formation, the catalyst may then be subjected to an appropriate regeneration procedure.

For purposes of the present invention, regeneration may be conducted in the following manner:

The reactor is heated in the presence of steam and air to about 750° F.–1000° F. for several hours. The reactor is subsequently cooled under an inert atmosphere, e.g., nitrogen.

EXAMPLES

The following non-limiting examples are given by way of illustration of the present invention.

Example I

The following example is representative of the process of the present invention as applied to a gas containing ethylene and acetylene which also includes arsine as an acetylene converter moderator.

Operating conditions with the preferred levels shown in parentheses are as follows:

| Temperature: | 80° F.–350° F. |
| --- | --- |
| | (120° F.–225° F.) |
| Pressure: | 100 psig–750 psig |
| | (300 psig–450 psig) |
| Space Velocity: | 500 v/hr./v–15,000 v/hr./v |
| | (800 v/hr/v–3,000 v/hr./v) |

Example II

The following example is representative of a procedure in accordance with the present invention which is believed to show that arsenic is transferred from the palladium sites to the catalyst base during regeneration.

Fresh Pd on $Al_2O_3$ catalyst was impregnated with arsenic to a variety of concentrations by contacting the catalyst with an aqueous solution of arsenic pentoxide and drying. Each impregnated catalyst was regenerated in a muffle furnace to simulate transfer of arsenic to the base. The acetylene hydrogenation ability of each regenerated catalyst was determined by passing a gas containing acetylene, hydrogen, ethylene, and nitrogen, activity as a function of temperature.

These results are tabulated below:

TABLE 2

| Effect of Arsenic Loading on Catalyst Activity | |
| --- | --- |
| Temperature °C. for 90% Acetylene Removal | Wt. % Arsenic on Catalyst |
| 57 | 0 |
| 58 | 0.5 |
| 60 | 0.75 |
| 65 | 1.15 |
| 67 | 1.25 |
| 69 | 1.40 |

The results indicate that no significant activity loss was observed until the arsenic concentration exceeded 0.75 wt. %. Above this level, the activity dropped rapidly. When the loading reached 2%, the activity will be unacceptable for a commercial operation.

The catalyst activity towards acetylene hydrogenation is evidenced by a drop in operating temperature from end-of-run (EOR), which is typically 250° F. to start-of-run (SOR) which is typically 120° F.

Also this example shows that greater than 1.25% permanently deactivates the catalyst but that a catalyst having an arsine content within the range of less than about 0.01% to about 0.75% is regenerable.

Accordingly, the arsenic does not tend to build up on the palladium sites causing catalyst deactivation.

Example III

As indicated above, it has been discovered that arsenic does not build up on the palladium sites of the catalyst because arsenic is transferred from the palladium sites to the catalyst base during regeneration. Therefore, the catalyst deactivation which may be experienced as a result of activity loss is due to coking and/or green oil formation which has been discovered to precede arsenic poisoning.

The following example is presented to evidence this phenomenon.

Operating conditions with the preferred level shown in parentheses are shown as follows:

| Temperature: | 80° F.–350° F. |
| --- | --- |
| | (120° F.–225° F.) |
| Pressure: | 100 psig–750 psig |
| | (300 psig–450 psig) |
| Space Velocity: | 500 v/hr./v–15,000 v/hr./v |
| | (800 v/hr/v–3,000 v/hr./v) |

The feed gas containing 1 ppb–2 ppb of arsine is passed over the catalyst at the preferred operating conditions. The temperature is progressively raised to compensate for the activity loss caused by green oil/polymer build-up. This results in a loss of selectivity. Eventually, the selectivity becomes unsatisfactory and this run is terminated. The arsenic loading is calculated to be much less than 0.75 wt.%, activity and selectivity can be recovered by regeneration. The process is then repeated.

The catalysts which are suitable for purposes of the present invention include: 0.01–0.5 wt % palladium on a support.

The preferred catalyst for purposes of the present invention, however, is a palladium-type hydrogenation catalyst, for example, palladium on alumina, which is selected for the hydrogenation of acetylene into ethylene in the presence of ethylene.

Example IV

The following example shows the effects of arsine treatment on acetylene converter performance. The data is depicted in the graph shown in FIG. 3.

Figure 3:
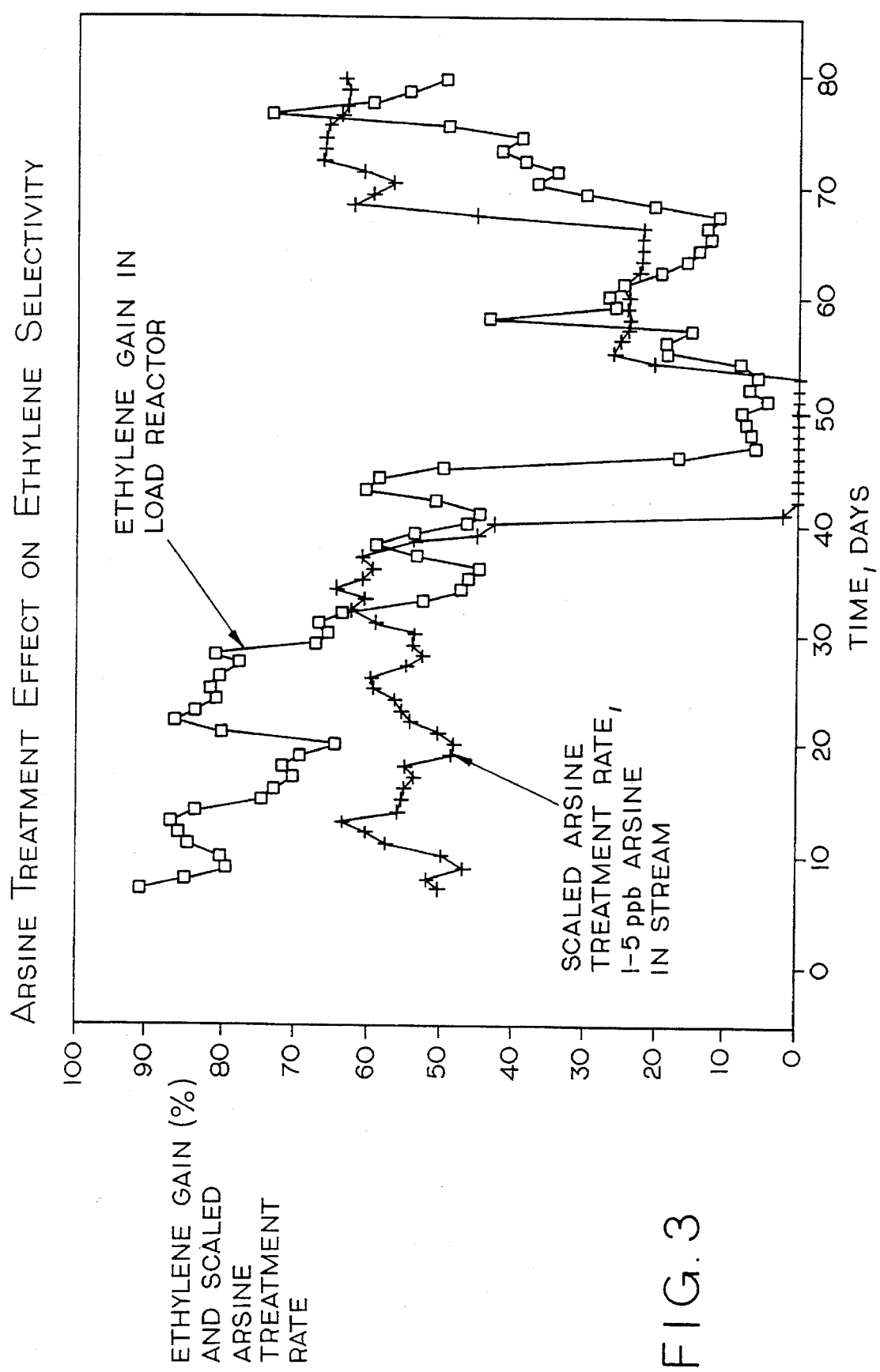
FIG. 3 is a graph showing the effect of arsine treatment on acetylene converter performance.

The operating parameters for the data shown in FIG. 3 are: GHSV: 4500–6000 V/V/HR; inlet temperature: 120°–160° F.; $H_2/C_2H_2$: 1.1 2.0.

As shown on the graph, the arsine treatment rate and the reactive selectivity to acetylene are compared. The selectivity is labeled acetylene gain. In acetylene converters, there are two competing reactions: i) acetylene reacts with hydrogen to form ethylene, and ethylene reacts with hydrogen to form ethane. The desired reaction is the reaction that forms ethylene. The ethylene gain is the net per cent of acetylene that forms ethylene.

Related to this, the following equation is used to calculate the ethylene gain:

$$\text{ethylene gain} = \frac{\text{Moles Ethylene Formed} - \text{Moles Ethylene Destroyed}}{\text{Moles Acetylene Reacted}} * 100$$

The graph in FIG. 3 shows results for approximately one quarter, i.e., about 80 days, of acetylene converter operation. As can be seen, the ethylene gain trends the arsine treatment rate very well. Before being removed completely, the ethylene gain showed slight variations corresponding to slight variations in the treatment rate. The effect was most noticeable when the treatment was completely removed. When the treatment was reapplied, the converter operation responded proportionately.

In general, the parameters suitable for purposes of the acetylene removal operation may be conventional. Particularly preferred for purposes of the present invention, however, are temperatures within the range of 50° F. to about 350° F.

Other parameters for practicing the present invention include the following:

|  | Suitable | Preferred | More Preferred | Most Preferred |
| --- | --- | --- | --- | --- |
| Inlet Temperature, °F. | 50–500 | 80–300 | 100–200 | 125–150 |
| GHSV, V/V/HR | 500–15000 | 1500–10000 | 2000–8000 | 4000–6000 |
| $H_2/C_2H_2$ | 1.0–10.0 | 1.0–3.0 | 1.0–2.0 | 1.0–1.5 |

It should be appreciated by those of ordinary skill in the art that, while the present invention has been described herein by reference to particular means, methods and materials, the scope of the present invention is not limited thereby, and extends to any and all other means, methods and materials suitable for practice of the present invention. Therefore, although the present invention has been described with reference to particular means, materials and embodiments, from the foregoing description, one skilled in the art can easily ascertain the essential characteristics of the present invention, and various changes and modifications may be made to various usages and conditions, without departing from the spirit and scope of the invention as described in the claims that follow.

What is claimed is:

1. A process for removing acetylene from a hydrocarbon stream, said process comprising:

exposing a hydrocarbon stream comprising acetylene to a hydrogenation catalyst in the presence of an acetylene converter moderator selected from the group consisting of arsine and phosphine in an amount within the range of about 0.01 wppb to about 10 wppb which is introduced into said stream and which substantially remains on said hydrogenation catalyst and does not substantially migrate into said hydrocarbon stream under conditions effective to support acetylene hydrogenation.

2. The process for removing acetylene from a hydrocarbon stream of claim 1, wherein said acetylene converter moderator is arsine.

3. The process for removing acetylene from a hydrocarbon stream of claim 2, wherein said amount of arsine is present within the range of about 1 wppb to about 3 wppb.

4. The process for removing acetylene from a hydrocarbon stream of claim 3, wherein said hydrogenation catalyst is exposed to said amount of said arsine by blending up to 1000 wppm arsine in a carrier gas.

5. The process for removing acetylene from a hydrocarbon stream of claim 4, wherein said blending is performed using a technique selected from the group consisting of a direct external injection technique and a controlled leakage technique.

6. The process for removing acetylene from a hydrocarbon stream of claim 5, wherein said technique is direct external injection.

7. The process for removing acetylene from a hydrocarbon stream of claim 6, wherein an amount less than about 400 ppm arsine is blended with said carrier gas.

8. The process for removing acetylene from a hydrocarbon stream of claim 7, wherein said amount is within the range of 10 ppm–400 ppm.

9. The process for removing acetylene from a hydrocarbon stream of claim 8, wherein said amount is about 200 ppm.

10. The process for removing acetylene from a hydrocarbon stream of claim 4, wherein said carrier gas is selected from the group consisting of ethylene, ethane nitrogen, helium, and argon and mixtures thereof.

11. The process for removing acetylene from a hydrocarbon stream of claim 10, wherein said gas is selected from the group consisting of argon and ethylene.

12. The process for removing acetylene from a hydrocarbon stream of claim 6, wherein said exposing comprising contacting said hydrogenation catalyst with said carrier gas containing about 100 wppm–20,000 wppm acetylene at a temperature with the range of about 80° F. to about 350° F., a pressure within the range of about 100 psi to about 750 psi and at an gas hourly space velocity of about 3000 v/hr./v. to about 15,000 v/hr./v. to control the amount of arsine on said hydrogenation catalyst to within the range of about 1 wppb to about 3 wppb.

13. The process for removing acetylene from a hydrocarbon stream of claim 12, whereby deactivation of said hydrogenation catalyst as indicated by a loss of catalyst activity occurs primarily due to coking, green oil formation, or a combination of coking and green oil formation and said loss of catalyst activity due to the presence of arsenic is substantially avoided.

14. The process for removing acetylene from a hydrocarbon stream of claim 13, further comprising regenerating said deactivated catalyst to restore at least some of said loss of catalyst activity due to said coking, said green oil formation or said combination of coking and green oil formation.

15. The process for removing acetylene from a hydrocarbon stream of claim 14, further comprising repeating said regenerating of said catalyst successively until said catalyst activity is reduced to an unacceptable level for a commercial operation due to said coking, said green oil formation, or a combination of coking and green oil formation.

16. The process for removing acetylene from a hydrocarbon stream of claim 15, wherein said unacceptable level of catalyst selectively loss due to said coking, said green oil formation or said combination of coking and green oil formation occurs before a permanent poisoning by arsenic.

17. The process for removing acetylene from a hydrocarbon stream of claim 16, wherein said hydrogenation catalyst comprises a transition metal selected from the group consisting of Group VIII metals, Group VIIIA metals and IB metals.

18. The process for removing acetylene from a hydrocarbon stream of claim 17, wherein said metal is palladium.

19. The process for removing acetylene from a hydrocarbon stream of claim 18, wherein said palladium is based on a support.

20. The process for removing acetylene from a hydrocarbon stream of claim 19, wherein said support comprises a support material selected from the group consisting of silica, zeolite, alumina, and a combination thereof.

21. The process for removing acetylene from a hydrocarbon stream of claim 20, wherein said support material is alumina.

22. The process for removing acetylene from a hydrocarbon stream of claim 21, wherein said regenerating results in transferring arsenic from palladium sites to said alumina.

23. The process for removing acetylene from a hydrocarbon stream of claim 3 wherein said hydrocarbon stream comprises a member selected from the group consisting of ethylene, and a mixture of ethylene and ethane.

24. The process for removing acetylene from a hydrocarbon stream of claim 23, wherein said hydrocarbon stream comprises steam cracker gas, catalytic cracker gas, ethylene and acetylene and is produced by a procedure selected from the group consisting of stream cracking, catalytic cracking, and coking.

25. The process for removing acetylene from a hydrocarbon stream of claim 23, wherein said conditions effective to support acetylene hydrogenation comprise a temperature within the range of about 80° F. to about 350° F., pressures within the range of about 100 psi to about 750 psi, and hourly space velocities within the range of about 3,000 to about 15,000 v/hr./v.

26. A method of producing an ethylene product comprising:

providing ethylene which is substantially devoid of acetylene and acetylene converter moderators wherein the acetylene has been removed by a process comprising exposing a hydrocarbon stream comprising ethylene and acetylene to a hydrogenation catalyst in the presence of an acetylene converter moderator selected from the group consisting of arsine and phosphine in an amount within the range of about 0.01 wppb to about 10 wppb which is introduced into said stream and which substantially remains on said hydrogenation catalyst and does not substantially migrate into said hydrocarbon stream under conditions effective to support acetylene hydrogenation; and utilizing said ethylene to produce a product comprising polyethylene.

* * * * *